(12) United States Patent
Bagha

(10) Patent No.: US 9,398,891 B2
(45) Date of Patent: *Jul. 26, 2016

(54) MULTIPLE COMMUNICATION INTERFACE MEDICAL EXAMINATION APPARATUS, SYSTEM, AND/OR METHOD

(75) Inventor: Merat Bagha, Portland, OR (US)

(73) Assignee: TIBA MEDICAL, INC., Plano, TX (US)

( * ) Notice: Subject to any disclaimer, the term of this patent is extended or adjusted under 35 U.S.C. 154(b) by 1468 days.

This patent is subject to a terminal disclaimer.

(21) Appl. No.: 12/054,385

(22) Filed: Mar. 24, 2008

(65) Prior Publication Data

US 2008/0232605 A1 Sep. 25, 2008

Related U.S. Application Data

(63) Continuation-in-part of application No. 11/584,236, filed on Oct. 20, 2006, now Pat. No. 8,092,396.

(60) Provisional application No. 60/919,594, filed on Mar. 24, 2007, provisional application No. 60/728,568, filed on Oct. 20, 2005.

(51) Int. Cl.
*A61B 5/02* (2006.01)
*A61B 7/00* (2006.01)
*A61B 7/04* (2006.01)
*A61B 5/00* (2006.01)
(Continued)

(52) U.S. Cl.
CPC .................. *A61B 7/04* (2013.01); *A61B 5/0002* (2013.01); *A61B 5/0245* (2013.01); *A61B 5/0472* (2013.01); *A61B 7/003* (2013.01)

(58) Field of Classification Search
CPC ...... A61B 7/04; A61B 5/0002; A61B 5/0245; A61B 7/003; A61B 5/0472
USPC ............. 181/131; 381/67, 509; 600/300, 513, 600/528, 586
See application file for complete search history.

(56) References Cited

U.S. PATENT DOCUMENTS 3,858,005 A 12/1974 Marshall et al.
4,248,241 A 2/1981 Tacchi
(Continued)

FOREIGN PATENT DOCUMENTS

DE 10132759 1/2003
FR 2768323 3/1999
(Continued)

*Primary Examiner* — Sean Dougherty
(74) *Attorney, Agent, or Firm* — Mateo Aboy; Aboy & Associates, PC

(57) ABSTRACT

An embodiment of an auscultation device can be constructed using, at least in part, electronic components to provide improved acquisition, processing, and communication of sound signals. An input device can be used for detecting sounds, and electrical signals representing the sounds can be processed and transmitted via one or more of a plurality of substantially contemporaneously available wired and/or wireless communications interfaces. Bluetooth and/or another form of wireless communication can be employed. Such embodiments can employ, at least in part, one or more of several commercially available wired and/or wireless receiver devices, such as, without limitation, headsets and headphones, mobile phones, PDAs and/or other handheld devices, desktop, laptop, palmtop, and/or tablet computers, speakers and/or other conventional and/or specifically configured computer devices and/or electronic devices.

6 Claims, 12 Drawing Sheets

(51) Int. Cl.
*A61B 5/0245* (2006.01)
*A61B 5/0472* (2006.01)

(56) References Cited

U.S. PATENT DOCUMENTS

| | | | |
|---|---|---|---|
| 4,723,555 A | 2/1988 | Shue | |
| 4,770,189 A | 9/1988 | Shyu | |
| 4,777,961 A | 10/1988 | Saltzman | |
| 4,878,501 A | 11/1989 | Shue | |
| 4,972,841 A | 11/1990 | Iguchi | |
| 5,025,809 A | 6/1991 | Johnson et al. | |
| 5,027,825 A | 7/1991 | Phelps, Sr. et al. | |
| 5,204,500 A | 4/1993 | Dufresne et al. | |
| 5,206,602 A * | 4/1993 | Baumgartner et al. | 330/9 |
| 5,218,969 A | 6/1993 | Bredesen et al. | |
| 5,360,005 A | 11/1994 | Wilk | |
| 5,409,010 A * | 4/1995 | Beach et al. | 600/455 |
| 5,663,532 A | 9/1997 | Dieken et al. | |
| 5,717,769 A | 2/1998 | Williams | |
| 5,737,429 A | 4/1998 | Lee | |
| 5,812,678 A | 9/1998 | Scalise et al. | |
| 5,825,895 A | 10/1998 | Grasfield et al. | |
| 5,844,995 A | 12/1998 | Williams | |
| 5,909,495 A | 6/1999 | Andrea | |
| 6,002,777 A | 12/1999 | Grasfield et al. | |
| 6,005,951 A | 12/1999 | Grasfield et al. | |
| 6,171,263 B1 | 1/2001 | Sullivan | |
| 6,236,862 B1 * | 5/2001 | Erten et al. | 455/501 |
| 6,244,376 B1 * | 6/2001 | Granzotto | 181/131 |
| 6,344,025 B1 | 2/2002 | Inagaki et al. | |
| 6,358,218 B1 | 3/2002 | Want et al. | |
| 6,396,931 B1 | 5/2002 | Malilay | |
| 6,533,736 B1 | 3/2003 | Moore | |
| 6,540,673 B2 | 4/2003 | Gopinathan et al. | |
| 6,544,198 B2 | 4/2003 | Chong et al. | |
| 6,757,392 B1 | 6/2004 | Granzotto et al. | |
| 6,852,084 B1 | 2/2005 | Boesen | |
| 7,346,174 B1 * | 3/2008 | Smith | 381/67 |
| 2001/0030077 A1 | 10/2001 | Watson | |
| 2001/0050992 A1 | 12/2001 | Carman | |
| 2002/0071570 A1 | 6/2002 | Cohen et al. | |
| 2002/0085724 A1 | 7/2002 | Grasfield et al. | |
| 2003/0002685 A1 | 1/2003 | Werblud | |
| 2003/0072457 A1 * | 4/2003 | Grasfield et al. | 381/67 |
| 2003/0102983 A1 | 6/2003 | Hsieh Hung | |
| 2003/0208130 A1 | 11/2003 | Yotam et al. | |
| 2004/0032957 A1 * | 2/2004 | Mansy et al. | 381/67 |
| 2004/0037429 A1 | 2/2004 | Candioty | |
| 2004/0068194 A1 * | 4/2004 | Johnson et al. | 600/508 |
| 2004/0076303 A1 | 4/2004 | Vyshedskly et al. | |
| 2004/0092846 A1 | 5/2004 | Watrous | |
| 2004/0096069 A1 | 5/2004 | Chien | |
| 2004/0157612 A1 | 8/2004 | Kim | |
| 2004/0203383 A1 * | 10/2004 | Kelton et al. | 455/41.2 |
| 2004/0220487 A1 | 11/2004 | Vyshedskiy et al. | |
| 2004/0220488 A1 | 11/2004 | Vyshedskiy et al. | |
| 2004/0223621 A1 | 11/2004 | Orten | |
| 2004/0225476 A1 | 11/2004 | Tien | |
| 2004/0228494 A1 * | 11/2004 | Smith | 381/67 |
| 2004/0249298 A1 | 12/2004 | Selevan | |
| 2005/0043642 A1 | 2/2005 | Sauerland | |
| 2005/0070811 A1 | 3/2005 | Crowley | |
| 2005/0074130 A1 | 4/2005 | Brummel et al. | |
| 2005/0083194 A1 | 4/2005 | Shen | |
| 2005/0090755 A1 | 4/2005 | Guion et al. | |
| 2005/0101843 A1 | 5/2005 | Quinn et al. | |
| 2005/0107715 A1 * | 5/2005 | Abbruscato | 600/528 |
| 2005/0119584 A1 | 6/2005 | Carter | |
| 2005/0148883 A1 * | 7/2005 | Boesen | 600/485 |
| 2005/0157887 A1 | 7/2005 | Kim | |
| 2005/0157888 A1 | 7/2005 | Yang | |
| 2005/0165310 A1 | 7/2005 | Bindefeld | |
| 2005/0203349 A1 | 9/2005 | Nanikashvili | |
| 2006/0047215 A1 * | 3/2006 | Newman et al. | 600/513 |
| 2006/0158344 A1 * | 7/2006 | Bambini et al. | 340/825.69 |
| 2006/0285696 A1 * | 12/2006 | Houtsma | 381/67 |
| 2007/0049838 A1 * | 3/2007 | Sauerland | 600/528 |
| 2007/0058818 A1 * | 3/2007 | Yoshimine | 381/67 |
| 2007/0106179 A1 * | 5/2007 | Bagha et al. | 600/586 |
| 2008/0037800 A1 | 2/2008 | Grasfield et al. | |
| 2009/0117526 A1 * | 5/2009 | Lecat | 434/266 |

FOREIGN PATENT DOCUMENTS

| | | |
|---|---|---|
| JP | 53149352 | 12/1978 |
| JP | 2004081250 | 3/2004 |
| JP | 2004261264 | 9/2004 |

* cited by examiner

MULTIPLE COMMUNICATION INTERFACE MEDICAL EXAMINATION APPARATUS, SYSTEM, AND/OR METHOD

RELATED APPLICATIONS

This application claims the benefit of priority from, and is a nonprovisional of, U.S. Provisional Patent Application No. 60/919,594, filed Mar. 24, 2007, and claims the benefit of priority from, and is a continuation-in-part of, U.S. patent application Ser. No. 11/584,236, filed Oct. 20, 2006, which claims the benefit of priority from and is a nonprovisional of U.S. Provisional Patent Application No. 60/728,568, filed Oct. 20, 2005, each of which are hereby incorporated by reference in their entirety.

COPYRIGHT NOTICE

© 2008 Tiba Medical, Inc. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71(d), (e).

TECHNICAL FIELD

Embodiments consistent with the present application relate to one or more auscultation methods, apparatuses, and/or systems for medical examination, testing, and/or diagnosis.

BACKGROUND

Auscultation techniques are useful for medical examination, testing, and diagnosis. Typically, auscultation involves a qualified medical practitioner listening to the internal sounds of a subject's body, usually using a stethoscope. Auscultation is normally performed to examine biological systems, such as the cardiovascular, respiratory, and/or gastrointestinal systems or humans and/or animals.

Traditionally, auscultation is a skill that requires substantial clinical experience, and an environment that permits clear hearing. Heart sounds, for example, can sound rather faint through an acoustic stethoscope. Tubes used to transmit acoustic sounds through traditional stethoscopes can create extraneous noise when the tubes rub against hands, body, or clothing, etc. Additionally, traditional stethoscopes poorly accommodate those with moderate to severe hearing loss, or those who work in noisy environments (e.g., emergency rooms, helicopters, etc.).

Another problem with many existing auscultation devices is that they are constructed of a metallic material. While metallic surfaces can substantially accommodate various sterilization procedures, they also can be cold to the touch when placed against the skin of a subject. They also can show poor resistance to moisture, thus being susceptible to water damage.

SUMMARY

Embodiments of an auscultation device can be constructed employing one or more electronic components, at least in part, to facilitate electrical processing and/or transmission of sound, including, without limitation, performing signal enhancement and/or communication functions. One embodiment of an auscultation device can transmit audio signals or sound data via one or more of a plurality of communications interfaces. Each of the plurality of communications interfaces can be used as alternatives to one another, or one or more of the plurality of communications interfaces can be used substantially simultaneously. Auscultation device embodiments can be constructed with an ergonomically sized and shaped casing that is comfortable for an operator to use. Similarly, one or more contact surfaces on the casing, which come into contact with the subject, can be constructed of a material that is easy-to-clean, waterproof or water resistant, and not cold to the touch.

An auscultation device embodiment can implement an input device and/or circuitry for detecting sound from the subject. The detected sound can be converted into an electrical signal, and a controller can be employed for processing the electrical signal, if, or to the extent that, such processing is desirable. Controller embodiments can employ digital signal processors and/or other processing logic to facilitate amplification, diagnosis, and/or selective filtering of electrical signals representing detected sounds. Embodiments can transmit a processed signal using one or more of a plurality of substantially contemporaneously implementable communications interfaces, to one or more of a plurality of correspondingly compatible receiving devices. Numerous commercially available wired or wireless receiver devices can be employed as a receiver, such as, without limitation, headsets and headphones, mobile phones, PDAs and/or other handheld devices, desktop, laptop, palmtop, and/or tablet computers, speakers, and/or other computer devices and/or electronic devices.

DETAILED DESCRIPTION

Figure 1:
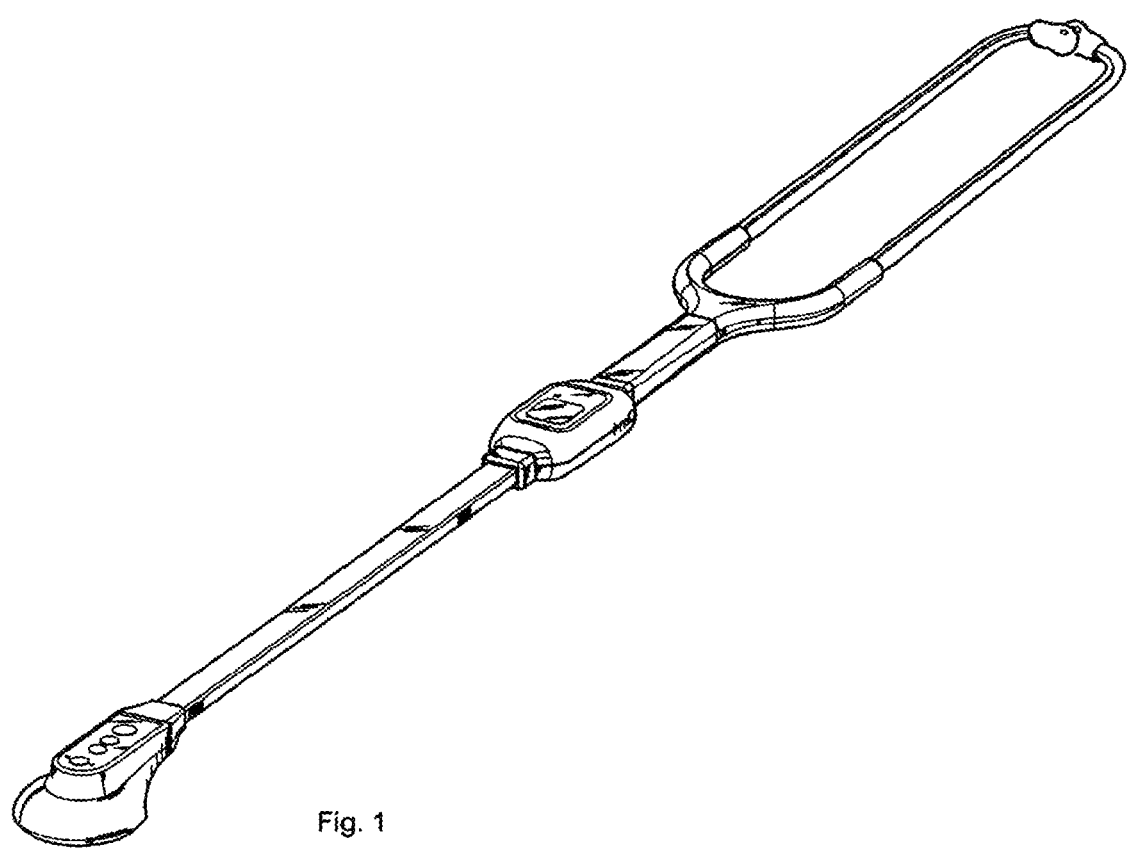
FIG. 1 illustrates an isometric view of a medical device for auscultation constructed in accordance with a first embodiment.
Figure 2:
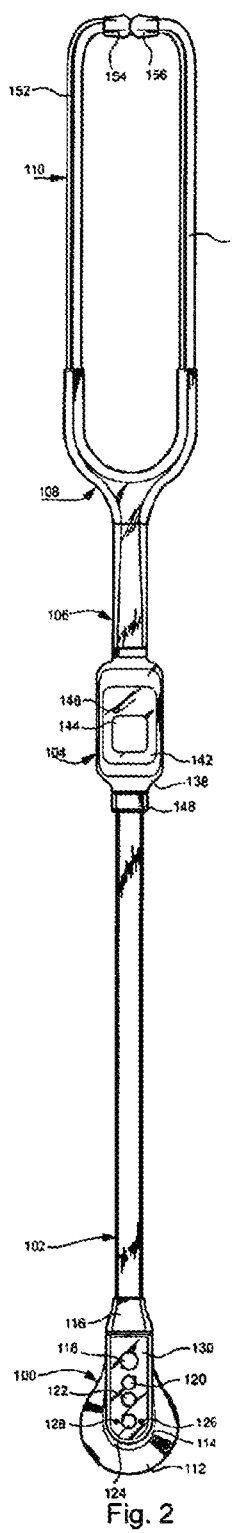
FIG. 2 illustrates a top view of the medical device embodiment illustrated in FIG. 1.
Figure 3:
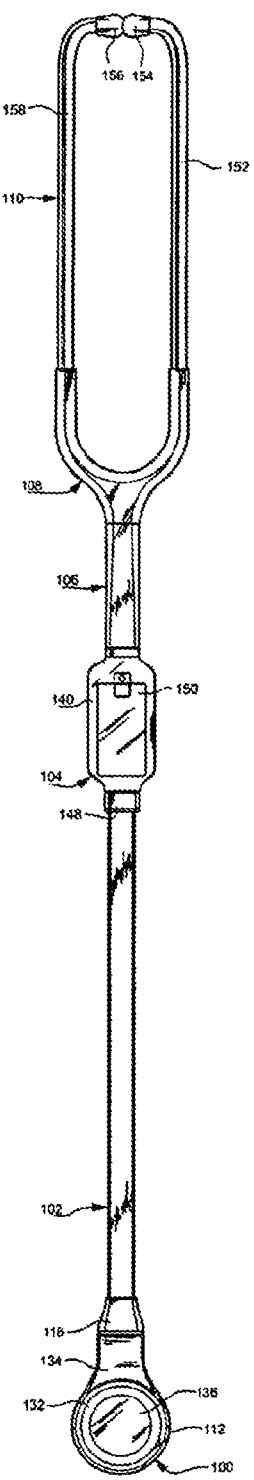
FIG. 3 illustrates a bottom view of the medical device embodiment illustrated in FIG. 1.
Figure 4:
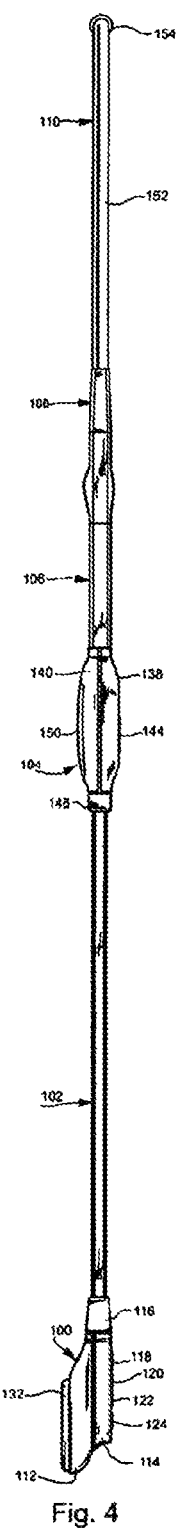
FIG. 4 illustrates a left side view of the medical device embodiment illustrated in FIG. 1.
Figure 5:
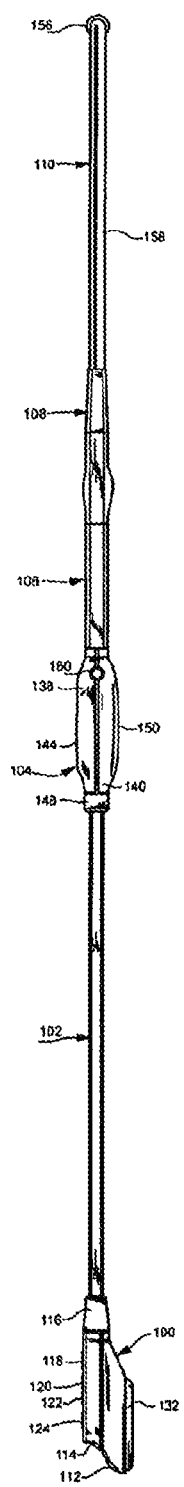
FIG. 5 illustrates a right side view of the medical device embodiment illustrated in FIG. 1.

In one embodiment, presented herein for illustrative purposes and without limitation, the claimed subject matter can encompass an auscultation device, such an electronic stethoscope, as but one example, to be used by physicians or other professionals to detect and/or monitor biological sounds of the body (human, animal, etc.) such as the heart or the lung. Embodiments consistent with the claimed subject matter can use one or more of a plurality of integrated communication interfaces substantially contemporaneously made available for selection and/or implementation by a user, either separately or in one or more combinations. In one embodiment, the plurality of communications interfaces can substantially encompass both wired and wireless communications interfaces. One such embodiment can use wireless Bluetooth® communications protocols and/or other wireless communications technology in addition to, or as an alterative to, electronic components offering substantially wired transmission of audio signals between the chest piece and ear piece of an auscultation device. Present embodiments can offer compatibility with various wireless protocols, including, without limitation, Bluetooth 1.2 and/or 2.0, and/or later specification standards, to list but a few examples. The claimed subject matter is not limited in this regard, however, as alternative or additional wireless standards can also be employed consistent with the claimed subject matter.

Embodiments can function with commercially available Bluetooth and/or other applicable wireless receivers including, without limitation, audio devices such as headsets and headphones, mobile phones, PDAs and/or other handheld devices, desktop, laptop, palmtop, and/or tablet computers, speakers, and/or other computer devices and/or electronic devices, as but a few examples. Custom designed, or variously commercially available software programs can be run on one or more devices communicating with the auscultation device, depending, at least in part on the requirements of the intended operating environment. Present auscultation device embodiments can also enable backchannel communications via Bluetooth or other transmissions for, at least in part, facilitating status reporting and/or other data transfer to a connected device. The claimed subject matter, however, is not limited to the illustrative characteristics described with respect to these embodiments. Alternative embodiments can employ additional or alternative receiver devices, standards, and/or technologies, now known or later developed, consistent with the claimed subject matter. For example, in addition or as an alternative to conventional devices, a specialized audio receiver device can be selected, constructed, and/or configured for functioning cooperatively with an auscultation device as described herein. One such device can be embodied as a hearing aid with integrated wireless receiver circuitry. For example, such an auscultation device embodiment can substantially include the ability to interface with hearing aids worn by healthcare professionals who have experienced at least some hearing loss. In such a case, the auscultation device can interface with the hearing aid via wired and/or wireless means directly, or indirectly through an intermediary device that allows the user to switch between hearing sounds from the ambient environment around them, the auscultation device, and/or another device, such as a telephone or music player, etc.

Auscultation device communications, whether wired, wireless, or a combination of both, can be configured to be substantially secure and reliable in various locations and/or operating environments, such as clinics, hospitals, and/or other settings where numerous types of equipment or alternate sources of potential signal interference can be present. In one example, an embodiment can be used by a doctor as part of a routine medical examination in an examination room of a medical office, as well as other potential locations. In another example, an embodiment can be used in a surgical room, or other location, as a pre-tracheal, precordial, and/or esophageal stethoscope or auscultation device, which can be used by an anesthesiologist to monitor for blocked air passages in the patient by listening to the patient's breathing sounds. In such an operating environment, an auscultation device offering, at least in part, wireless communications can help allow the anesthesiologist to reduce one or more sub-optimal effects of having a physical device connecting them and the patient, even while the anesthesiologist still remains in the room and attends to the patient during the procedure/operation. However, in certain implementations, or for select users, the look and feel of a more traditional stethoscope may still be considered desirable. In such cases one or more embodiments can additionally or alternatively include the ability to transmit signals via wired communications interfaces to, as but one example, a headset through one or more audio connections. Such audio connections can include, for example, a substantially standardized 3.5 mm audio jack, or an integrated electronic earpiece, as but two examples presented for illustrative purposes and not by way of limitation. An alternative embodiment can employ a 2.5 mm audio jack, at least in part, to accommodate wired headphones and/or other devices having a 2.5 mm connector. Another substantially wired communications interface can encompass an audio speaker integrated into the auscultation device to transmit audio signals to a user's ear, such as in a loudspeaker application, or via communication to a user through ear buds integrated into, connected to, and/or otherwise made available with the auscultation device. Additional and/or alternative communications interfaces, and sound or data transmission mechanisms could also be employed consistent with the present subject matter. Embodiments that allow the user to choose wired and/or wireless communications methods can offer increased flexibility to the user.

Embodiments employing electronic components that enable signal processing can offer amplification, diagnosis, and/or filtering of detected sounds, as but a few examples. By enabling signal processing, embodiments can, for example, help accommodate or assist those with moderate hearing-loss or those who work in noisy environments (e.g., emergency rooms, helicopters, etc.). Such embodiments can help produce improved sound quality (e.g., sound quality that is sharper, crisper, and clearer, etc.), thus enabling better diagnosis of a patient's condition.

An auscultation device consistent with one embodiment of the present technology may include, at least in part, a chest piece with an integrated microphone and a plurality of wired and/or wireless communications interfaces that are substantially concurrently available and alternatively and/or cooperatively selectable for implementation by a user. FIGS. 1-22 illustrate one embodiment of an auscultation device and corresponding component embodiments consistent with the claimed subject matter. The auscultation device and illustrated component embodiments of FIGS. 1-22 are depicted for illustrative purposes only, and their illustration is not meant to serve as a limitation on the type, quantity, and/or configuration of potential components encompassing an auscultation device consistent with the claimed subject matter.

One embodiment of an auscultation device can include the ability to interface with wired and/or wireless receivers such as an earpiece, headset, headphone, PC, PDA, tablet computer, speaker, and/or other computer and/or electronic device, among others. Embodiments offering flexibility in the communications method and type and/or style of receiver employed can substantially offer advantages to users. For example, a user that has an in-the-ear hearing aid can choose to use a wireless over-the-ear style headset as the receiver, thus improving comfort.

Presently disclosed embodiments can achieve improved sound amplification while also including an auscultation device that can, at least in part, support both bell and diaphragm modes (e.g., enabling heart and lung examination, etc.), either separately or in combination. For example, and without limitation, one embodiment can support frequency ranges such as 20-200 Hz for bell mode operation, 100-500 Hz for diaphragm mode operation, and/or 20-1000 Hz for a combined bell/diaphragm mode operation.

One embodiment consistent with the claimed subject matter can offer improved sound transmission. For example, an embodiment can offer improved sound amplification. For example, embodiments can be provided that can produce signals enhanced to approximately 40 times or 50 times that of traditional stethoscopes. These magnitudes of enhancement, however, are presented for illustration only, and not by way of limitation. The claimed subject matter is not limited in this regard. An auscultation device can be engineered to alternate amplification parameters selected, at least in part, to satisfy the intended use and/or operating environment for the embodiment. Alternative embodiments can achieve alternate levels and/or ranges of sound amplification. An embodiment providing electronic amplification can aid a user in examining a patient such as, for example, an obese individual having a lot of fatty tissue, which can make listening to heart and lung sounds difficult. Embodiments of the present technology can also allow for the filtering of ambient sounds and artifacts such as hand motions and/or contact with body hair. In one example, which is presented for illustrative purposes and not by way of limitation, an embodiment can exhibit signal-to-noise characteristics consistent with one or more specified ranges (e.g., greater than 88 decibels, etc.). However, alternate embodiments can exhibit alternate signal-to-noise characteristics and/or varying operable ranges.

For illustrative purposes and for facilitating disclosure, reference will be made herein to the embodiments illustrated in the drawing figures. It should be noted however, that these embodiments and their respective component embodiments are presented for illustrative purposes only, and not by way of limitation. Additional and/or alternative embodiments and/or component embodiments can also be employed consistent with the claimed subject matter. Beginning the discussion with reference to FIGS. 1-22, one embodiment of an auscultation device can include a chest piece component 100 (as well as any of several compatible, separate receiver components, which are not depicted) and a battery compartment component 104, either and/or both of which can include a casing that can be sized, shaped, formed, and/or constructed so as to be easily and/or comfortably grasped and manipulated by an operator during use.

Figure 8:
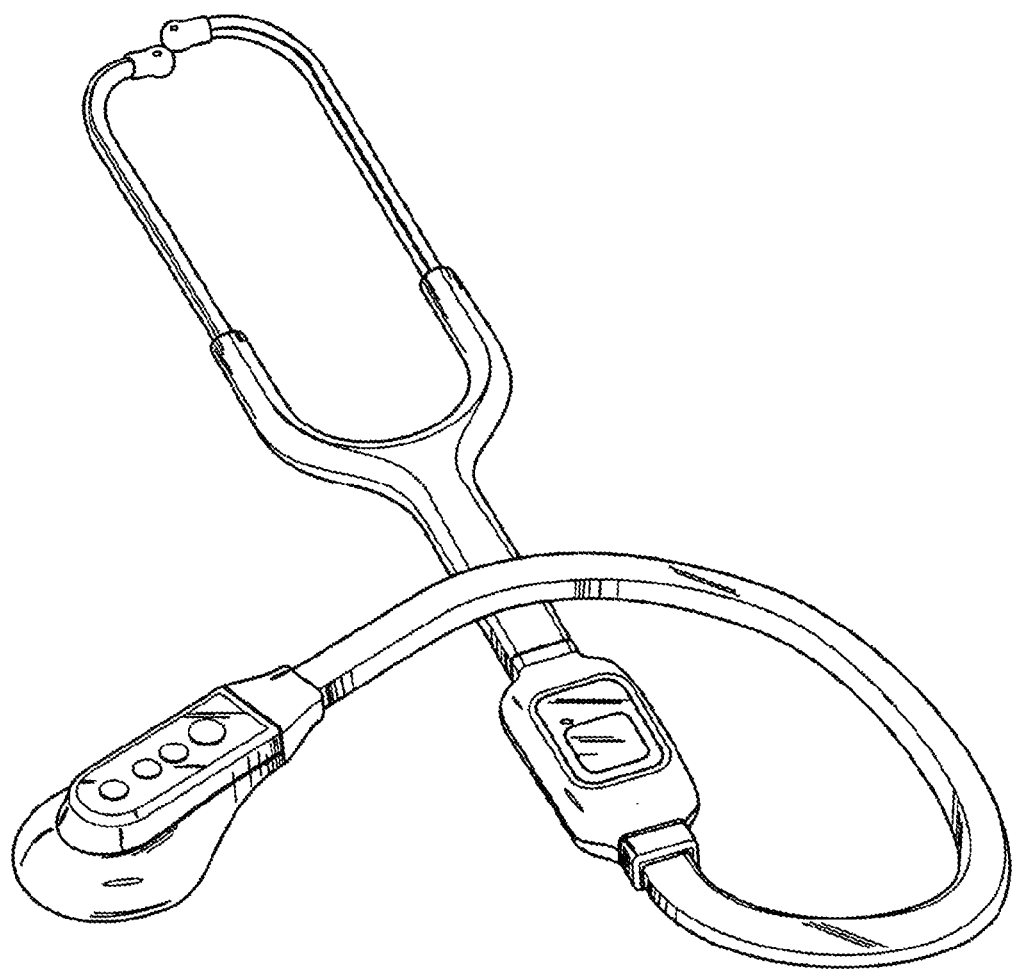
FIG. 8 illustrates an isometric view of the medical device embodiment illustrated in FIG. 1, implementing at least one substantially flexible portion and being arranged in an alternate position and/or configuration.
Figure 6:
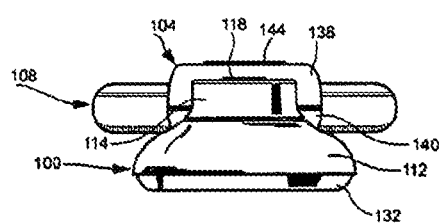
FIG. 6 illustrates a front end view of the medical device embodiment illustrated in FIG. 1.
Figure 7:
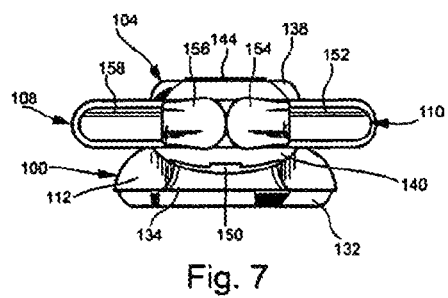
FIG. 7 illustrates a rear end view of the medical device embodiment illustrated in FIG. 1.
Figure 9:
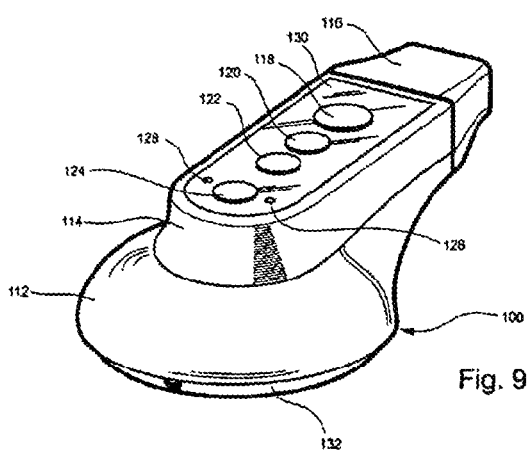
FIG. 9 illustrates a detailed, close-up isometric view of a chest piece component of the medical device embodiment illustrated in FIGS. 1-8.
Figure 10:
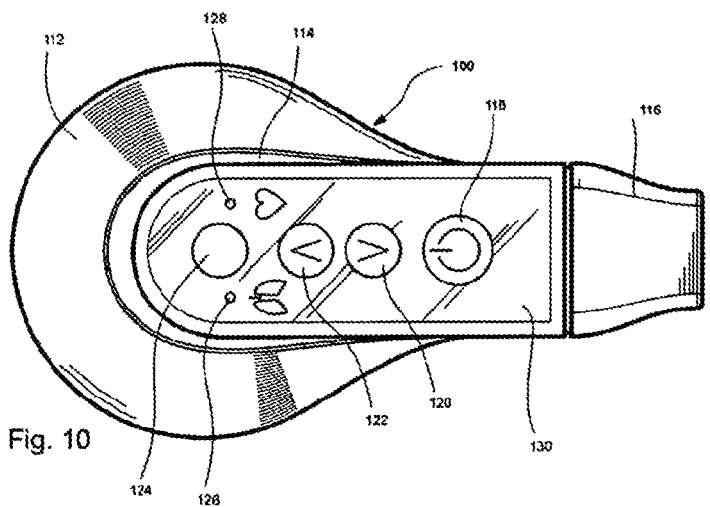
FIG. 10 illustrates a detailed, close-up top view of a chest piece component of the medical device embodiment illustrated in FIG. 1.
Figure 11:
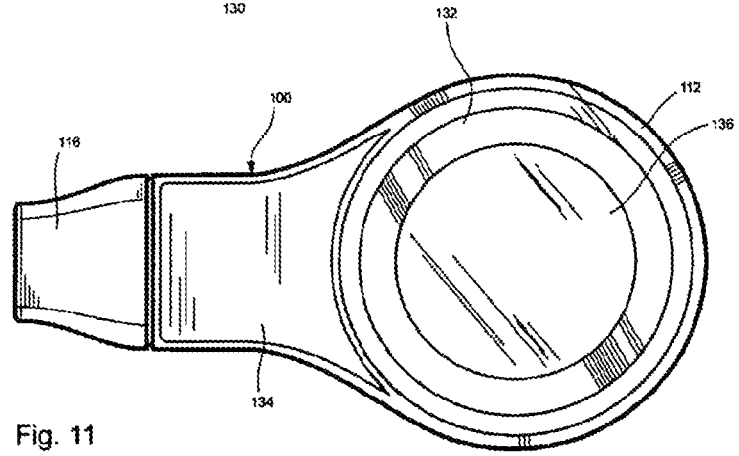
FIG. 11 illustrates a detailed, close-up bottom view of a chest piece component of the medical device embodiment illustrated in FIG. 1.
Figure 12:
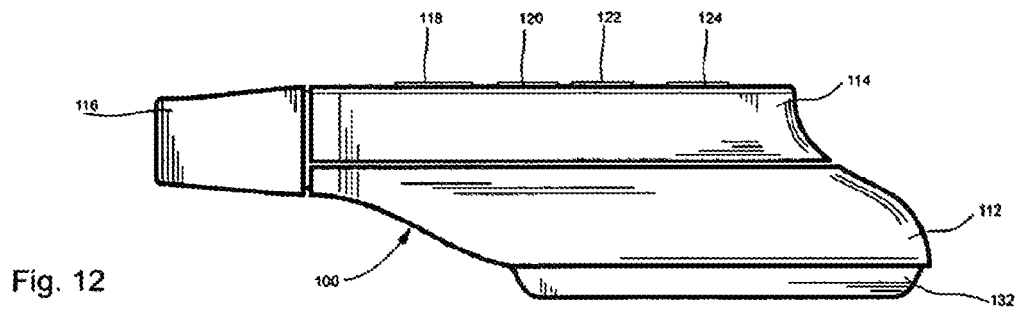
FIG. 12 illustrates a detailed, close-up left side view of a chest piece component of the medical device embodiment illustrated in FIG. 1.
Figure 13:
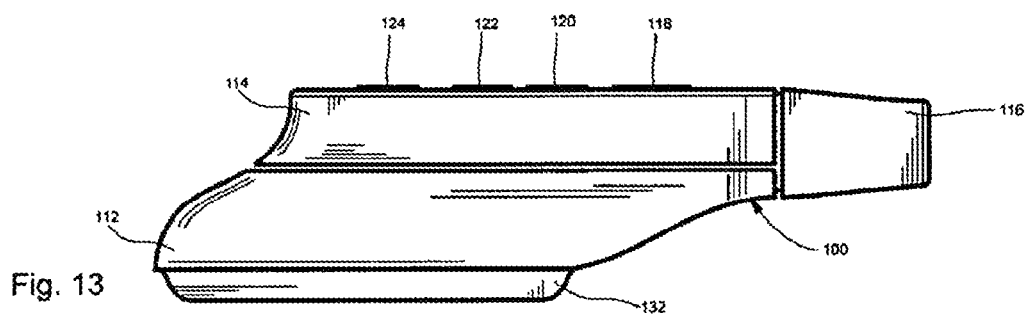
FIG. 13 illustrates a detailed, close-up right side view of a chest piece component of the medical device embodiment illustrated in FIG. 1.
Figure 14:
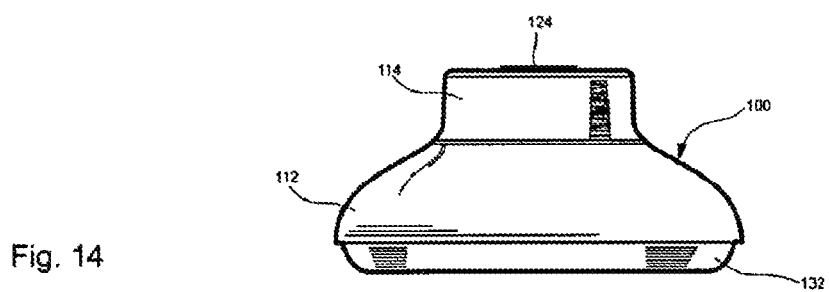
FIG. 14 illustrates a detailed, close-up front end view of a chest piece component of the medical device embodiment illustrated in FIG. 1.
Figure 15:
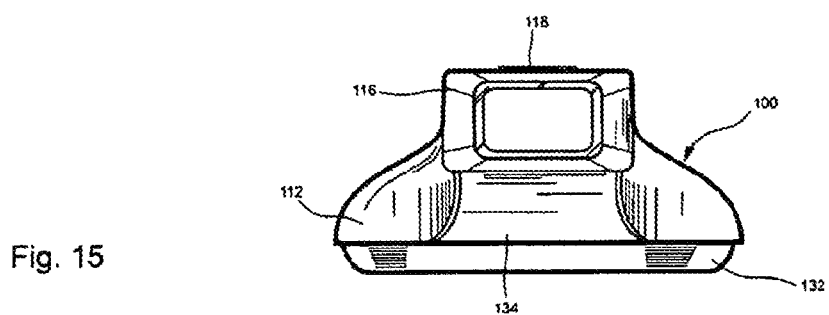
FIG. 15 illustrates a detailed, close-up rear end view of a chest piece component of the medical device embodiment illustrated in FIG. 1.
Figure 16:
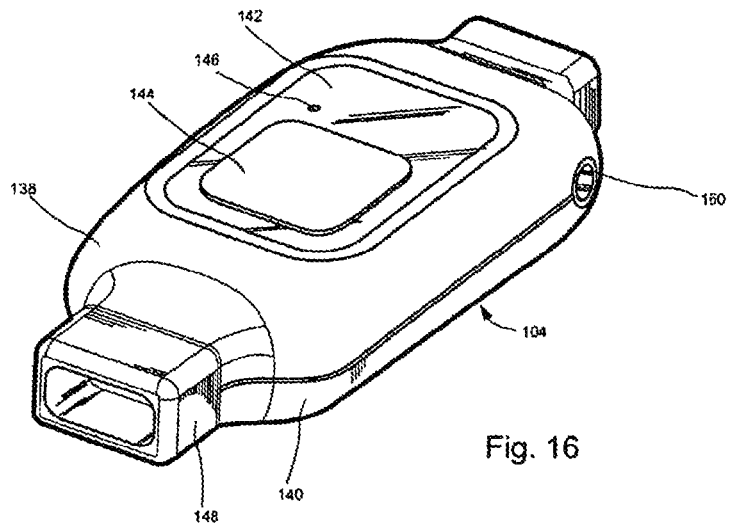
FIG. 16 illustrates a detailed, close-up isometric view of a battery compartment component of the medical device embodiment illustrated in FIGS. 1-8.
Figure 17:
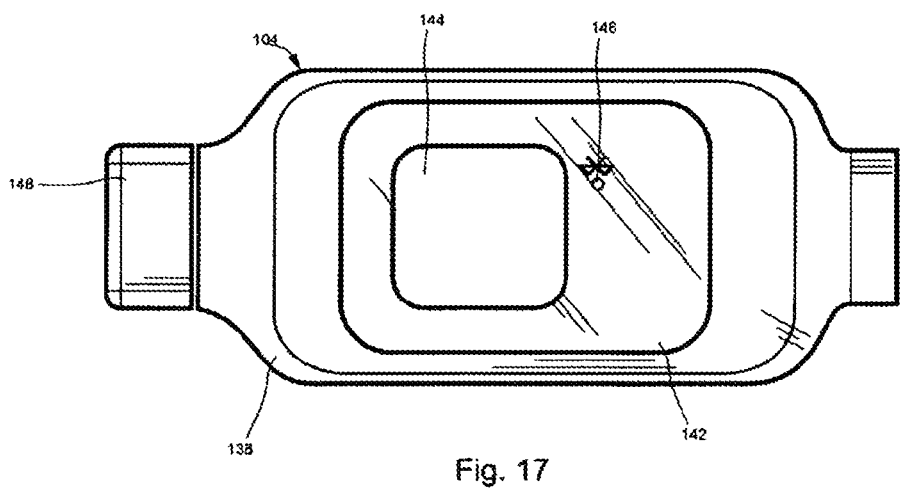
FIG. 17 illustrates a detailed, close-up top view of a battery compartment component of the medical device embodiment illustrated in FIG. 1.
Figure 18:
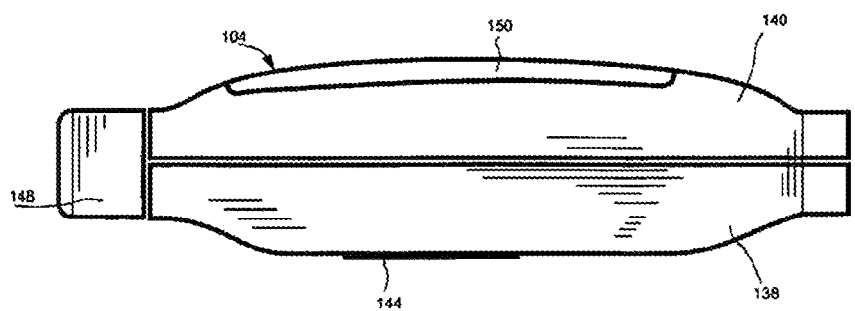
FIG. 18 illustrates a detailed, close-up left side view of a battery compartment component of the medical device embodiment illustrated in FIG. 1.
Figure 19:
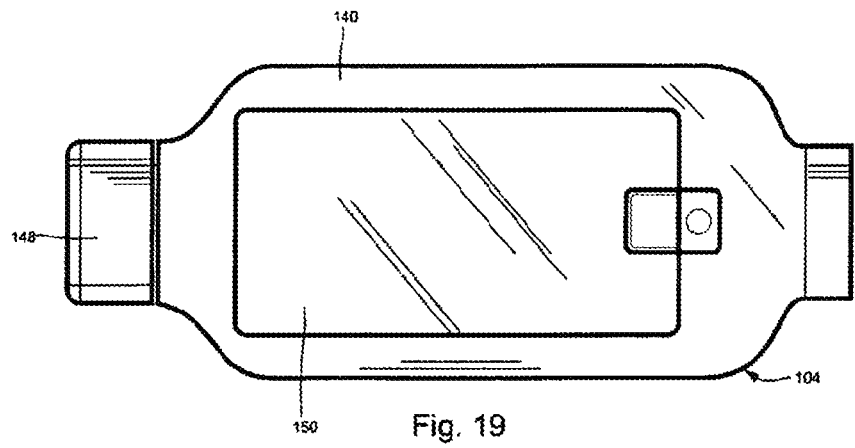
FIG. 19 illustrates a detailed, close-up bottom view of a battery compartment component of the medical device embodiment illustrated in FIG. 1.
Figure 20:
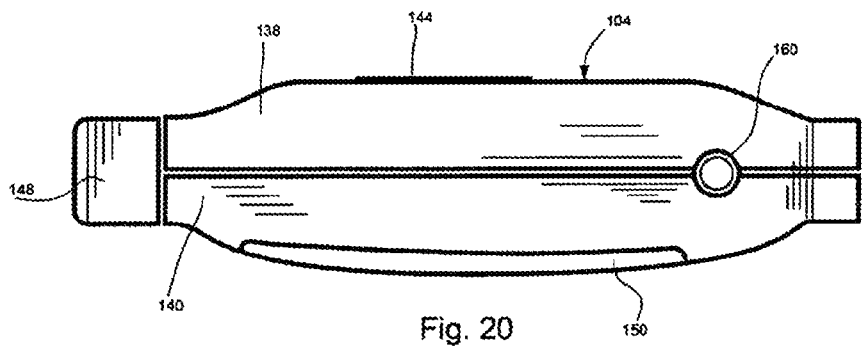
FIG. 20 illustrates a detailed, close-up right side view of a battery compartment component of the medical device embodiment illustrated in FIG. 1.
Figure 21:
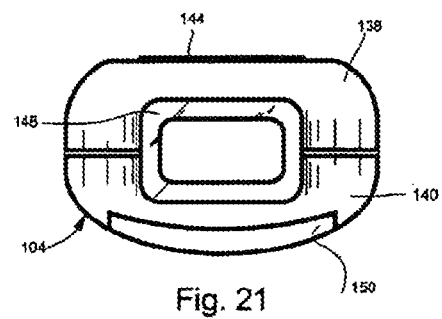
FIG. 21 illustrates a detailed, close-up front end view of a battery compartment component of the medical device embodiment illustrated in FIG. 1.
Figure 22:
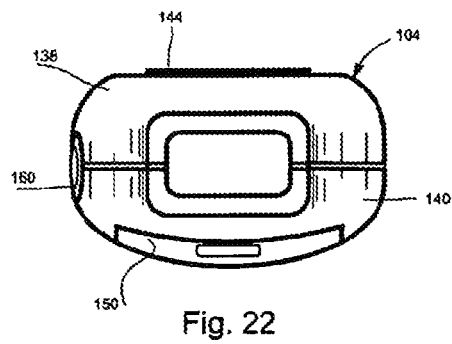
FIG. 22 illustrates a detailed, close-up rear end view of a battery compartment component of the medical device embodiment illustrated in FIG. 1.

With particular reference to FIGS. 1-22, FIG. 1 depicts an isometric view of one auscultation medical device embodiment consistent with the claimed subject matter. FIGS. 2-7 highlight various components and their cooperative configuration, positioning, and/or integration to encompass the auscultation device of FIG. 1. FIGS. 2-7 depict top, bottom, left side, right side, front end, and rear end view, respectively of the embodiment illustrated FIG. 1. Such a device embodiment can employ a configuration that provides improved functionality relative to traditional auscultation devices, while maintaining a familiar "look and feel" that is reminiscent of traditional devices. Such an embodiment can include a chest piece component 100 connected to a battery compartment component 104 via a first transmission conduit 102. Battery compartment component 104 can be connected via a second transmission conduit 106 to a Y-tube 108, which can provide transmission of detected auscultation sounds through a binaural transmission section 110 to ear buds 154 & 156, which are positioned into the user's ears during operation. In one embodiment, binaural transmission section 110 can include metal tubes 152 & 158, as but one example. FIG. 8 illustrates the auscultation device embodiment of FIG. 1 in one of several possible alternate configuration achieved, at least in part, by employing substantially flexible material in the construction of the first transmission conduit 102 of FIG. 1.

As one example of an alternative embodiment, a user can decide to selectively listen via the ear buds 154 & 156 by selectively attaching or detaching a portion of the device that includes ear buds 154 & 156 from a remaining portion of the device that detects and generates the auscultation signals. For example, the battery compartment end of the second transmission conduit 106 can be detached and reattached from the battery compartment component 104. Such an embodiment can employ couplings similar and/or analogous to those used by audio earpieces coupling with an audio port. Such a coupling can provide a combined mechanical/electrical coupling (e.g., a twist or snap in place connection) that both retains the second transmission conduit 106 connected to the battery compartment component 104, and provides an electrical connection to facilitate transmission of the auscultation signals electrically to speakers provisioned in ear buds 154 & 156, or from a speaker provisioned in or near battery compartment component 104 or Y-tube 108, through an air void in conduit/ tubes in the binaural transmission section 110, to ear buds 154 & 154. These are but a few examples of alternative embodiments consistent with the claimed subject matter.

FIGS. 9-15 illustrates a detailed, close-up views of chest piece component 100 of the medical device embodiment illustrated in FIGS. 1-8. In particular, FIGS. 9-15 illustrate isometric, top, bottom, left side, right side, front end, and rear end views of chest piece component 100. With particular reference to FIGS. 9-15, chest piece component 100 can encompass a housing including a chest piece over-mold 112, a chest piece control housing 114, a chest piece strain relief 116, a power control 118, volume controls 120 & 122, an auscultation mode selection control 124, display embodiments such as LED light pipes providing a bell auscultation mode indicator 126 and diaphragm auscultation mode indicator 128. Chest piece component 100 can also include a chest piece control input plate 130, diaphragm seal 132, chest piece bottom housing cover 134, and diaphragm component 136. Of course, those skilled in the relevant art will appreciate that additional, fewer, and/or alternative components can also be employed consistent with the claimed subject matter.

FIGS. 16-22 illustrates a detailed, close-up views of battery compartment component 104 of the medical device embodiment illustrated in FIGS. 1-8, depicted in isometric, top, left side, bottom, right side, front end, and rear end views respectively. With particular reference to FIGS. 16-22, battery compartment component 104 can encompass a battery housing top 138, a battery housing bottom 140, a battery housing control plate 142, a wireless communications control 144, a display element such as an LED light pipe 146 providing a wireless communications status indication, a battery compartment strain relief 148, and a door/access panel 150.

For illustrative purposes, and not by way of limitation, one embodiment of a chest piece component 100 can include at least some of the electronic components used to assemble an auscultation device that is operable consistent with the claimed subject matter. Examples of component embodiments can include a cap, a top cover, a printed circuit board (PCB) assembly, a housing, a mass, a microphone gasket, a microphone, a diaphragm, and a diaphragm seal. Although the auscultation device embodiment illustrated in FIGS. 1-22 depicts a battery compartment component 104 as separate from the chest piece component 100, an alternative embodiment could integrate a battery compartment, rechargeable battery, and/or alternative power source into the chest piece component 100. Of course, those skilled in the relevant art will appreciate that fewer, additional, and/or alternative components could be used in the construction of an auscultation device consistent with the claimed subject matter, depending at least in part on the desired implementation.

In further illustration of a chest piece component 100 consistent with the claimed subject matter, and to describe a relative interrelation and/or placement of the included electronic component embodiments, a cap embodiment can be bonded, welded, painted-on and/or otherwise affixed (substantially temporarily or substantially permanently) to top cover embodiment. A microphone embodiment can be inserted into gasket embodiment, which in turn can be inserted into mass embodiment. Similarly, the mass embodiment can be inserted into a housing embodiment as part of the assembly. In one embodiment a power source embodiment can be provisioned within a housing embodiment. A power source embodiment can be provisioned substantially securely within housing embodiment by using ribs, detents, protrusions, or insets, as but a few examples, integrated into the formation of housing embodiment. Also, a PCB assembly embodiment can be provisioned within the housing. The PCB assembly can also have a controller embodiment, a wireless interface embodiment, and one or more display embodiments, as well as an embodiment of one or more user input controls. A cap embodiment and a top cover embodiment can be coupled to a housing embodiment. Such components can be coupled via welding, screw thread mechanisms, and/or other means, depending, at least in part, on whether it is desired that the assembly be substantially permanently or substantially temporarily assembled. A diaphragm embodiment can be provisioned in relative cooperation with a housing embodiment. A diaphragm seal embodiment can also be coupled to a housing embodiment to substantially securely maintain the position of a diaphragm embodiment within the housing embodiment. An embodiment of a diaphragm seal can be coupled via threaded attachment to a housing embodiment, and/or affixed via other methods know to those skilled in the relevant arts. One embodiment of a device configured with components such as those mentioned above can be found in U.S. patent application Ser. No. 11/584,236, filed Oct. 20, 2006, which is hereby incorporated by reference in its entirety.

Auscultation device embodiments consistent with the claimed subject matter can employ a battery power source and exhibit an overall ergonomic construction with one or more aspects that are designed to be compact, light-weight, rugged, and/or durable. An auscultation device can be accompanied by an optional cradle that can provide convenient storage and/or a power source or interface for recharging rechargeable batteries. An embodiment can also include a headphone or other receiver. In one example, a receiver embodiment can be provided that can cooperate functionally with the auscultation device. A receiver embodiment can be provided substantially to match, approximate, and/or complement the ergonomics, design elements, and/or other aspects of the auscultation device. Batteries used in embodiments can be selected to provide a sufficient operating life to meet expected operating requirements of the user (e.g., batteries can provide a sufficient charge for 18 hours of continuous operation, etc.). One embodiment can also include an auto-off function to preserve battery life when the device is not in use for some predefined amount of time (e.g., one, two, three, minutes, or other time intervals, etc.). Embodiments can use commercially available rechargeable batteries which can be easily changed and/or recharged via intelligent and rapid charging. Embodiments using rechargeable batteries can support sufficient charge/recharge cycles as determined per user requirements (e.g., batteries can be charged/recharged for a year or more, etc.). Batteries can also be replaced after their effective life, but a battery compartment cover of the embodiment can be securely held in place so that it will resist detachment from the device if the device is dropped. One embodiment of a battery charger can operate in the range of 90-240 VAC, 50/60 Hz, for example, although alternate/additional operating ranges can be exhibited/enabled for operation in various geographic locations and/or environments.

An auscultation device embodiment's electronics may encompass a printed circuit board having programmable memory that will facilitate a variety of additional or alternate functionality. For example, an auscultation device may include onboard memory for recording and storing measurements. The auscultation device can also include a built-in speaker or audio jack to enable the playing of sounds either in real-time, or via playback from memory. When incorporated with a loudspeaker, such as a wired audio speaker and/or Bluetooth-based wireless loudspeaker, as but two examples, embodiments can broadcast detected sounds for multiple individuals to hear. Such embodiments can be useful, in one example, in environments where multiple people can be present, such as multiple medical practitioners, colleagues, family members, observing students, etc. Current or stored readings (which can be stored in a memory module onboard the PCB) can also be transmitted via wired or wireless connection to a computer or other receiver device for recording and/or analysis. An auscultation device employing any of various communications interfaces can also take advantage of one or more networks to transmit examination information over potentially long distances. For example, one embodiment can include a chest piece that can wirelessly transmit examination information to a Bluetooth-enabled mobile phone, which in turn can transmit the received signal over one or more wireless phone networks to an end user at a remote location.

Figure 24:
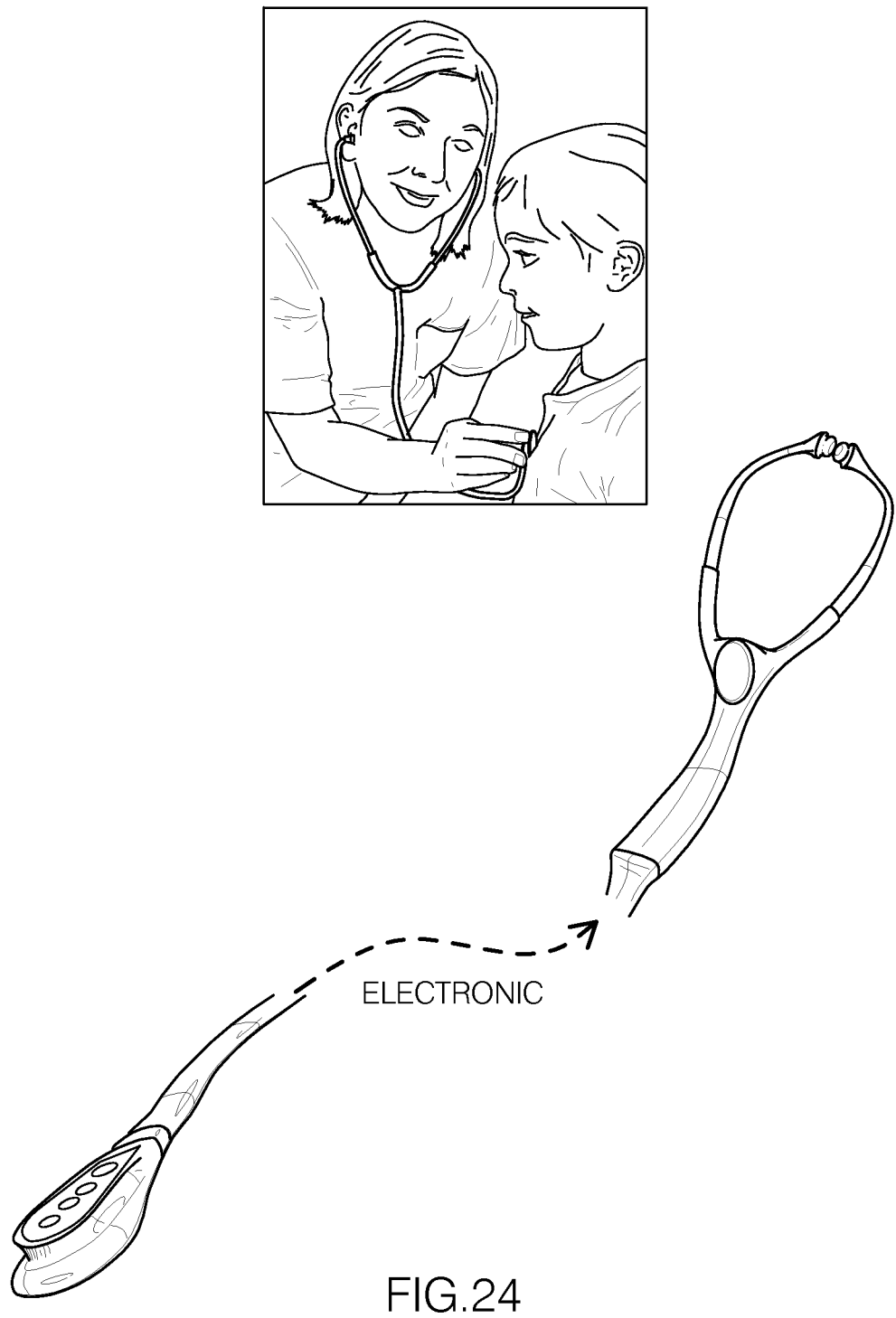
FIGS. 24-27 illustrate alterative embodiments of operating environments and/or configurations of an auscultation device and/or auscultation system consistent with the present subject matter.

FIGS. 24-27 illustrate four illustrative usage scenarios employable as, at least in part, auscultations systems consistent with the claimed subject matter. FIGS. 24-27 illustrate but a few of the potential system configurations implementable by a user via selecting one, or a combination, of the communications interfaces contemporaneously available with present auscultation device embodiments, together with one or more corresponding receivers and/or transmission devices/mechanisms. For example, FIG. 24 illustrates a system whereby auscultation sounds are transmitted electronically from a chest piece to ear buds. Such a configuration can satisfy users who prefer a device with a configuration reminiscent of traditional stethoscopes, while the electronic transmission can still provide advantages such as providing clear, crisp heart and lung sounds (bell, diaphragm, or combination modes), which can be amplified (either a variable/controlled amount, or fixed amount e.g., 40×, etc., as but one example) beyond their natural audible level. Such a system configuration can also be preferable in noisy environments or with users who have at least some hearing loss.

Figure 25:
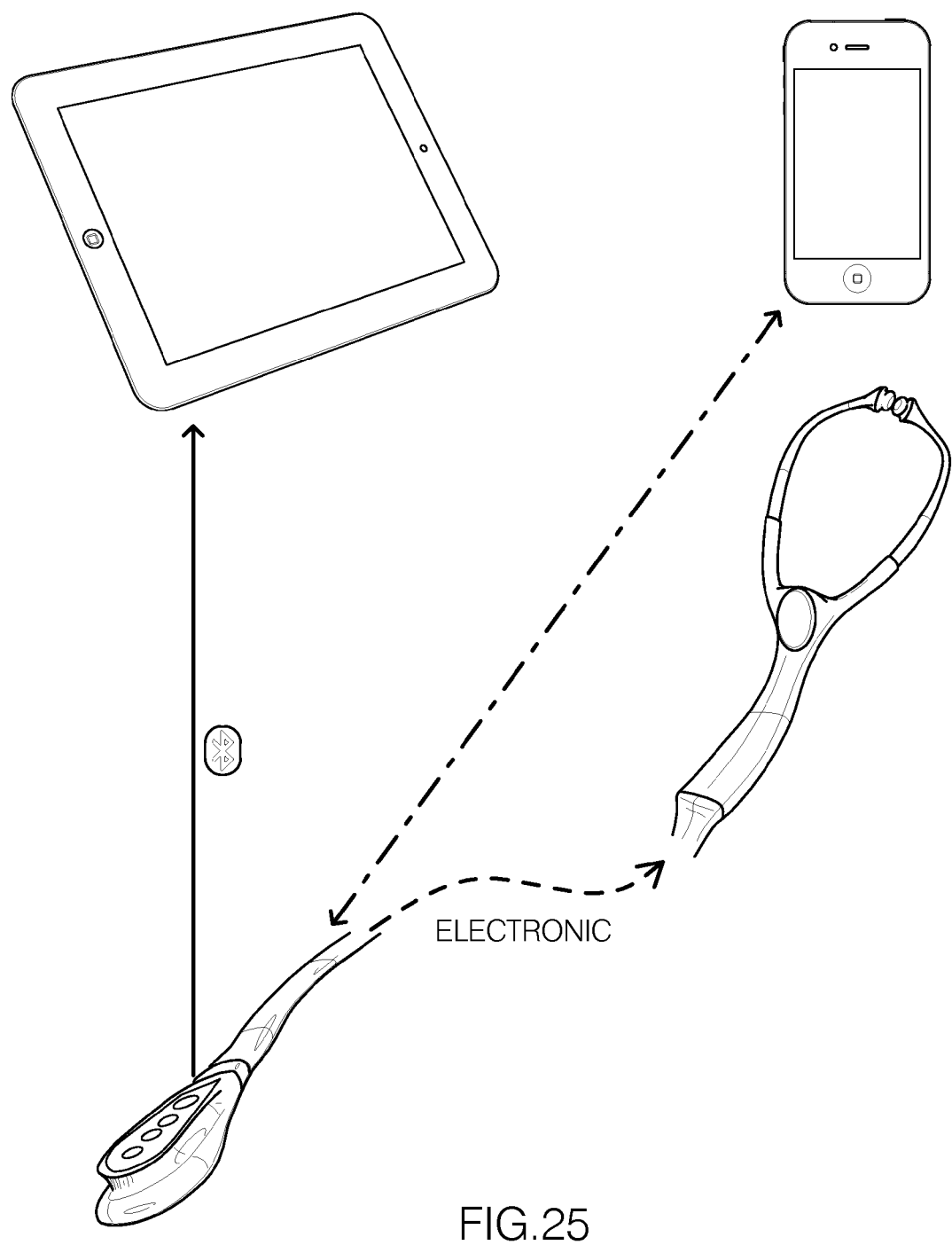

The system configuration embodiment illustrated in FIG. 25 illustrates the contemporaneous use of multiple communication interfaces. In the illustrated example configuration, a doctor or other primary user can receive auscultation sounds electronically transmitted via a wired interface, such as illustrated in FIG. 24, while one or more other users can receive real-time auscultation data and/or sounds wirelessly on a tablet PC, PDA, display device, and/or other computer or peripheral device via Bluetooth and/or other communications protocols (e.g., serial communications, Bluetooth wireless communications via Advanced Audio Distribution Profile (A2DP), etc.). Such a system configuration can facilitate real-time substantially contemporaneous listening by multiple users. Such a system configuration embodiment can facilitate substantially real-time wave form visualization, recording of auscultation data for future analysis or reference, and/or backchannel serial control via software on a peripheral device, to list but a few potential advantages.

Figure 26:
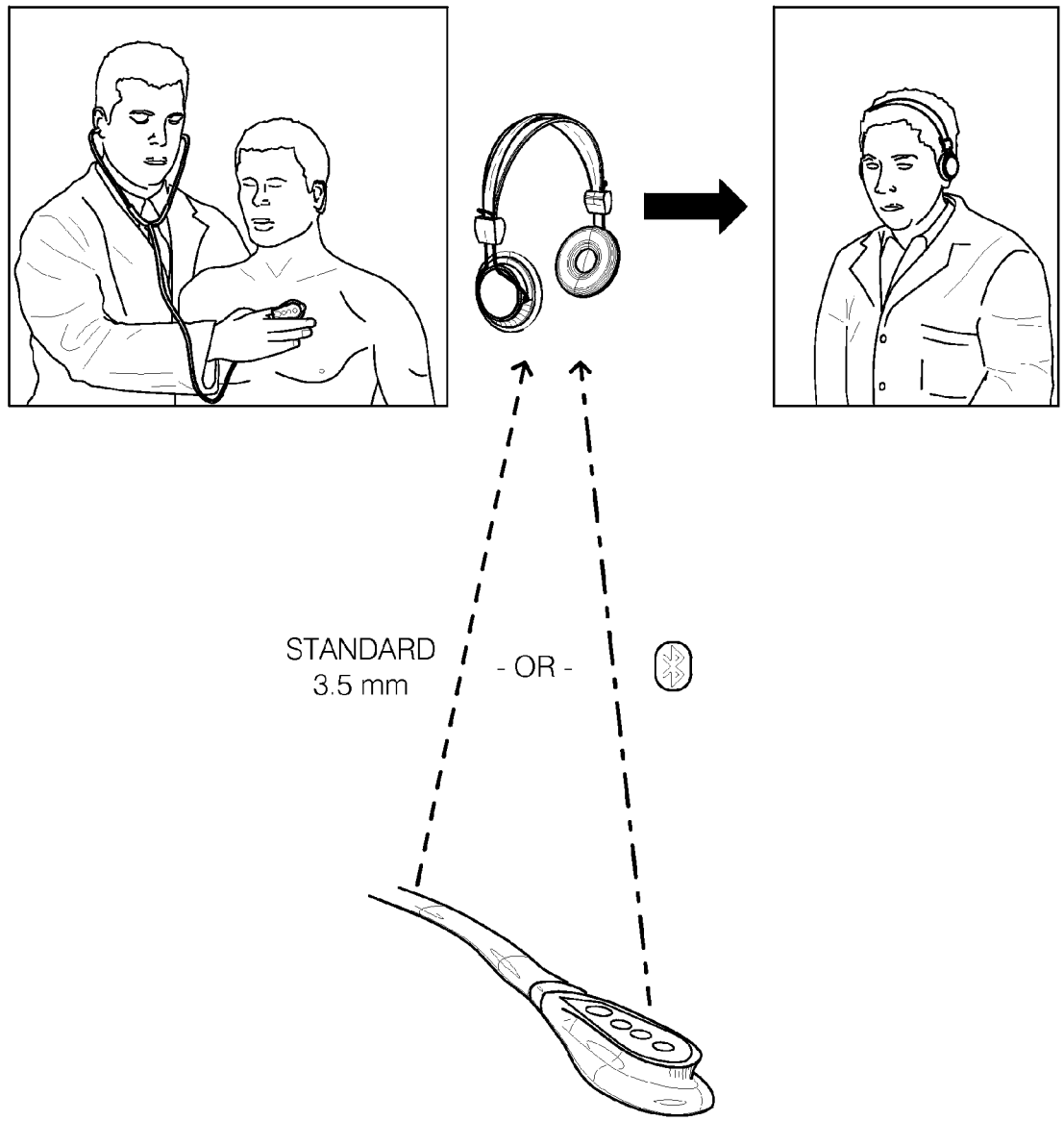

FIG. 26 illustrates an auscultation system having an alternative configuration to that illustrated in FIG. 25, while still providing communication of auscultation sounds substantially contemporaneously via multiple interfaces. As illustrated in FIG. 26, one user can listen via ear buds receiving signals via wired, electronic transmission, while one or more other users can substantially contemporaneously listen using standard wired (3.5 and/or 2.5 mm, etc.) or wireless (Bluetooth, etc.) headsets. Systems can also offer additional customization, such as facilitating a user in selecting from among multiple available/enabled forms of wireless communications (e.g., infrared, Wi-Fi, or Bluetooth) and/or selecting a particular profile for data transmission (e.g., allowing the user to select Advanced Audio Distribution Profile (A2DP), Headset Profile (HSP), etc. for Bluetooth communications).

Figure 27:
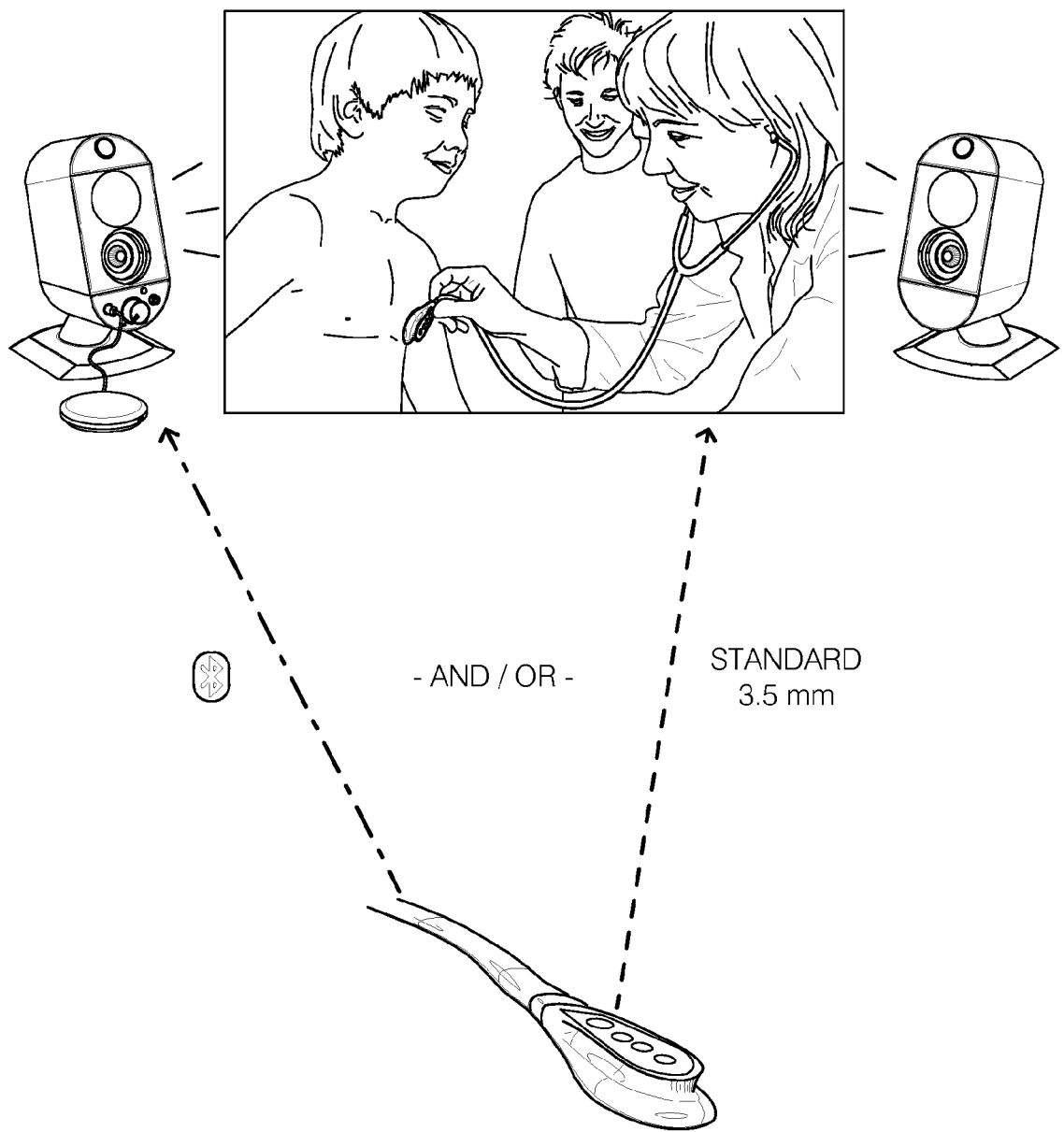

To illustrate yet an additional alterative system configuration embodiment, FIG. 27 presents an auscultation device employed to communicate auscultation sounds via wired (3.5 and/or 2.5 mm, etc.) and/or wireless (Bluetooth, etc.) audio speakers. Such a system configuration embodiment can facilitate real-time substantially contemporaneous listening by a group of users, improve therapy results with audio diagnosis support, and improve patient treatment and the patient experience by sharing the patient's auscultation sounds with the patient and/or the patient's family, support group, and/or caretakers, to list but a few benefits and advantages.

An auscultation device consistent with the claimed subject matter may also wirelessly transmit readings, or include an LED, LCD, or other onboard display, for displaying pulse rate information or QRS heart rhythm information, measured using two or three ECG leads, which may be built into a chest piece component, for example. Such displays can present information in a textual, graphical, symbolic, and/or other form. An embodiment with an on-board display and/or one or more controls, such as buttons, for example, can be designed so that the displays and/or controls can be viewed and accessed at a variety of angles and in varying light conditions, ranging from high to low levels of direct or indirect, natural or artificial light.

Auscultation device embodiments can be constructed to meet pertinent safety, environmental, and/or regulatory standards (including those promulgated by the United States FDA, FCC, and/or IEC, as well as the European CE Mark authorities or other agencies/regulatory bodies) that can govern the intended use of an embodiment. Embodiments consistent with the claimed subject matter can also exhibit a variety of characteristics that can offer operating advantages for the intended user or patient. For example, one embodiment, which is described by way of illustration and not as a limitation on the claimed subject matter, can be designed for functionality within a pre-specified operation set of operating parameters, such as an operating temperature range (e.g., –20-+50 degrees Celsius, etc.), a storage temperature range (e.g., –40-+70 degrees Celsius, etc.), an operating humidity range (e.g., 10-90 percent relative humidity, etc.), a storage humidity range (e.g., 10-95 percent relative humidity, etc.), operation within specification up to predefined altitudes (e.g., 10,000 feet, etc.), operation within specification at pressures up to a predefined level (e.g., 1 atm., etc.). Embodiments can also accommodate additional and/or alternative limits, ranges, and/or operating parameters consistent with the claimed subject matter.

In one embodiment, patient contact surfaces can be latex free, comfortable to the touch when contacting the patient (e.g., reduce use of metal and/or other cold contact surfaces), and/or easily cleaned and sanitized (e.g., with isopropyl alcohol and/or other material). A variety of commercially or industrially available polymer materials and/or engineering resin materials can be selected and used in the construction of an embodiment because they exhibit these desirable performance characteristics. For example, in one embodiment the casing of a chest piece can be made of an engineering resin equivalent to polycarbonate ABS or ABS. As another example, a diaphragm embodiment of a chest piece contact surface can be constructed of an engineering resin such as polycarbonate or glass filled nylon, listed here by way of example only, and not by way of limitation. Accordingly, even if a steel drum is provisioned under the diaphragm to help capture and resonate sound, implementing the engineering resin material on the contact surface of the diaphragm allows the chest piece to exhibit improved comfort for subjects being examined.

For reliability and quality control in wireless operating conditions, embodiments can include an alarm or other indicator for signaling when an apparatus is out of range of one or more of its intended wireless receivers. Embodiments can also include control features so that measurements are not provided under suboptimal conditions, such as low battery power, high EMI, etc., to name but a few examples. Devices consistent with the claimed subject matter can be constructed to as to be substantially waterproof and/or water resistant. An embodiment can also be durably constructed to as to resist tampering or disassembly by users, while still enabling easy manufacturing and servicing. An embodiment can be engineered so as to need reduced or no calibration during the lifetime of the device. An embodiment can also provide for personalization (e.g., such as by including a physical space to customize a device by displaying a name of the user/owner, etc.) and display of unique identification marks, for quality/control or security purposes (such as by including a serial number and/or other identifying information on the embodiment).

It should also be appreciated that an embodiment consistent with the claimed subject matter can include functionality in addition to the functions previously mentioned. For example, an embodiment can include a blood flow ultrasonic Doppler for such purposes, among others, as studying cardiac movements, arterial flow, fetal sounds, stomach, stomach, intestine, bowel and renal activity, as well as air-emboli, to represent but a few potential uses.

Consistent with the claimed subject matter, embodiments can encompass one or more devices incorporating, at least in part, substantially user-friendly designs, ergonomics, and controls. In one embodiment, a device can include multiple controls (e.g., such as buttons, switches, thumbwheels, joysticks, etc., to name but a few examples). By way of illustration, FIGS. 9-15 depict, in relative detail, one embodiment of a chest piece 100 exhibiting embodiments of multiple user input controls 118-124. FIGS. 9-15 also illustrates one embodiment of using substantially ergonomic contours in the design of chest piece embodiment 100.

Consistent with the claimed subject matter, an embodiment can encompass one or more controls 118-124 that can be used to control functionality for turning power on/off 118, increasing/decreasing volume 120 & 122, selecting an operating mode 124 (e.g., lung, heart, or combination examination, etc.), activating/deactivating a speaker, and/or controlling wireless or other electronic communication interfaces and/or data transmission mechanisms (e.g., input control 144 of FIGS. 16-22), as well as other purposes. An alternate embodiment can integrate multiple types of controls, and thus implement varied functionality, through a single and/or integrated combination control, using press-and-hold, multi-press, or alternative operation. Another embodiment can use on-board processing ability to identify and diagnose specific heart, lung, and/or other sounds and present information to a user. Such an embodiment can provide an improved ability for automatic diagnosis.

Embodiments can also include one or more visual display elements. Display embodiments can include on-board displays such as, for example, LEDs, LCDs, etc. On-board displays, or remote displays, wired or wirelessly linked to a measurement/examination device, can provide information including one or more indications of battery level, operating mode, volume level, pulse value, and/or QRS information (which can be presented in graphical form), among others. In alternate embodiments, multiple indicators can be integrated into one or more combined displays using, for example and without limitation, LCDs and/or multi-color LEDs employing either steady or flashing illumination states.

Figure 23:
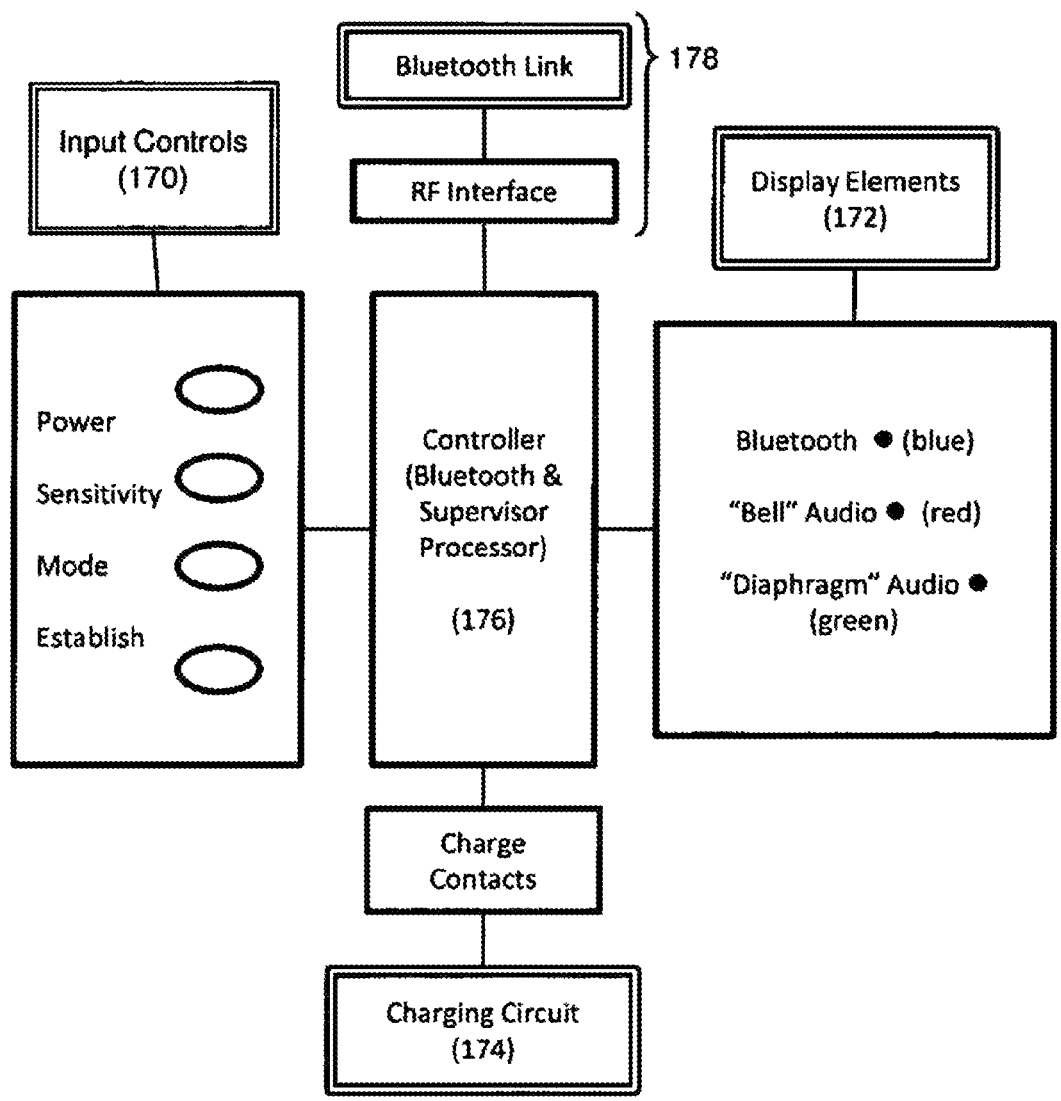
FIG. 23 illustrates an embodiment of a user interface block diagram consistent with the claimed subject matter.

FIG. 23 conceptually illustrates a user interface block diagram of one embodiment consistent with the claimed subject matter. In the embodiment of FIG. 23, multiple physical interfaces are shown for allowing a user to interact with a device. Interface embodiments can, in part, select and/or adjust various features and/or states of a device embodiment. As but a few examples presented for illustration, and not by way of limitation, interfaces can be embodied as input controls 170 to control engage, disengage, select, deselect, adjust, modify, alternate, and/or other wise control various features of a device, visual display elements 172 (e.g., LEDs, LCD, etc.) can be capable of displaying current status and/or other information related to a device, a wireless communications interface 178, such as a link to a Bluetooth antenna and/or other RF interface to enable connection to one or more other devices, and a charging circuit interface 174 employing electrical contacts to connect an external power source to a device. Consistent with the claimed subject matter, a controller embodiment 176, such as a Bluetooth and supervisor processor, for example, can be employed by a device to manage the various available interfaces.

One or more embodiments can enhance the user experience by offering a variety of advantageous features. For example, embodiments can provide features for, without limitation, power, listening, sensitivity, mode, wireless connection, wireless role, wireless pairing, and/or battery/power aspects of apparatuses, systems, and/or devices embodying the claimed subject matter. Embodiments described herein can include wireless functionality employing one or more Bluetooth specification standards, as well as additional and/or alternate wireless specifications, now know or later developed.

In one embodiment of a battery/power feature, an embodiment of a device can be in one of two power states: on or off. This state can be controlled by a power input button input button or through an automatic power off feature. To turn the device on, the user can press the power button 118. One or both of the mode display LEDs 126 & 128 can be lit to signal to the user that the device is in a power-on state. To turn the device off, a user can press and hold the power button 118 for a predetermined period of time, e.g., a predefined number of seconds, etc., as but one example). Any existing feature or function currently in use can be cancelled and/or terminated to complete the power-off function. When the power is off, all LEDs 126, 128, & 146 can remain off. This state can also be entered through an empty-battery-feature state. An automatic power-off feature can be provided so that the device automatically turns off after a predetermined period of time, or in response to some other identifiable condition, such as a device malfunction. This can help the device reduce power consumption. In an alternate embodiment, a device can provide for an extended-power-on feature to facilitate prolonged use. For example, if the automatic power-off feature is programmed to turn the device off after a set number of seconds, pressing the power button while the device is powered on can reset the counter for the power-off feature. Such a feature can help allow the user to extend the listening feature.

One embodiment of a Listening feature can help provide for detection, amplification, and transmission of one or more audio tones originating in the body of a human or other patient. One embodiment of a device can alternate between listening states. For example, a embodiment can be in an active state if it's power is on and the Bluetooth or other connection feature is in a connected state. An active state may be visually represented by through one or more displays on the device, such as by illuminating a connection/wireless communication LED and one or more mode LEDs, as but one example. In the active state, the embodiment can transmit audio tones, through one or more of a plurality of communications interfaces, to one or more user listening devices and/or receivers. Alternatively, an embodiment may be in an idle state when the power is on and the connection feature is in a disconnected state. A disconnected state can be visually communicated to the user through one or more display functions, such as by not illuminating a connection LED but illuminating one or more mode LEDs, for example. In an idle state, an embodiment can forgo transmission of audio tones.

One embodiment of a sensitivity feature can allow the user to change the gain of the input audio circuitry. An embodiment can employ a preset and/or predefined range of acceptable values, and a default sensitivity can be defined as residing approximately in the middle of the range values or at some other predefined value. In one embodiment, a user can change the sensitivity of a device by selecting a predetermined control, e.g., by pressing a select button, etc. Multiple controls can be included to adjust sensitivity levels, or a single control can be used. As one example of a single-control embodiment, each press of a button or other control by the user can increase the sensitivity one increment toward a maximum value. When the maximum sensitivity and/or volume is reached, a subsequent press of the control can return the sensitivity level to its minimum value. An embodiment can evidence sensitivity levels though audible tones or other methods. Change in sensitivity does not have to be indicated through one or more visual displays; however, such displays may be include in alternate embodiments as such modifications are equally consistent with the claimed subject matter.

One embodiment of a mode feature can, at least in part, help a user to tailor an audio processing mode of a device, depending on the needs of the desired diagnosis. Three examples of modes can include "bell," "diaphragm," or "wide." Bell mode, for example, can transmit audio frequencies for the audio tones used for heart sounds. Diaphragm mode, for example, can transmit audio frequencies suited for the audio tones used for lung sounds. A wide mode can be defined to encompass both bell and diaphragm modes. A user can press a mode button or other control until the embodiment is active in a desired mode. Mode status can be indicated through use of a common display, such as a multi-color LED with a different being used to represent each mode. Alternatively, a separate LED or other display can be provided to represent each mode, with the embodiment alternating between activation of the alternate displays, depending on the mode of the device as selected by the user (e.g., a user can press a mode button until a "bell" indicator LED is illuminated, etc.). To help simplify the design of embodiments of the claimed subject matter, at least in part, displays such as indicator LEDs showing the mode state of a device can also provide additional information, such as conveying the power state of the device (e.g., "bell" and "diaphragm" LEDs can also indicate the current states of the Power and Battery features, etc.) When an embodiment first powers up, it can be programmed to enter a default mode, such as bell mode for example. Last-known operating settings can be stored in onboard memory.

Consistent with the claimed subject matter, one embodiment of a communications interface can facilitate transmission of audio tones to any of several compatible user listening devices. In one embodiment, a Bluetooth connection feature can exist in varying states. As two examples, the connection feature can be connected or disconnected. A "connected" Bluetooth connection can be active when a device is turned on and it has an active communication connection. A connection LED can be illuminated once a connection has been created. Alternately, a "disconnected" Bluetooth connection state can be active when a device is turned on and no connection exists, which, in one embodiment, can be a result of the states of the Bluetooth role and Bluetooth pairing features describe below. In a disconnected state, a connection LED can remain off.

One embodiment of a Bluetooth role feature can help allow a device to assume one or more specific roles during connection establishment. For example, a Bluetooth role can be in an "initiator" or "acceptor" state, in addition to other states that can be defined for role assignment. The initiator of the Bluetooth connection starts the connection establishment. An embodiment in an initiator state can be programmed to create a connection with its one or more paired devices automatically when the power is supplied. If the device is unpaired, it can forgo creating a Bluetooth connection. In the initiator state embodiment, a device can function as a master (in a master-slave context). In the "acceptor" state, the Bluetooth connection feature can wait until another device initiates the establishment of a connection. If the device is unpaired, it can again forgo creating and/or allowing a connection. In the acceptor state embodiment, a device can function as a slave. To change the Bluetooth role state, the user can press and release the establish button and/or operate an alternate control interface. For example, a user can press and release the specific control button to set the initiator state. In one embodiment the absence of a button press for a predetermined amount of time can set the acceptor state. For effective communications and/or data integrity, embodiments can limit the user from substantially changing the Bluetooth role feature while engaged in active listening with the device. An alternate embodiment can provide a chest piece embodiment, for example, as well as one or more additional and/or alternate system components, which can function in a master and slave role substantially simultaneously. For example, one embodiment may include a tablet computer embodiment that can function as a mater to a chest piece embodiment slave, while the chest piece embodiment can substantially simultaneously be functioning as a master to a headphone receiver embodiment slave, as but one example.

An embodiment of "Bluetooth pairing" can include the process of forming a persistent relationship between two Bluetooth devices. This can allow a device to form a connection with a paired device with reduced user interaction. Bluetooth pairing typically occurs at least once between the examination/measuring device and the end user device listening device or receiver. Embodiments can also allow Bluetooth pairing to re-occur as desired. In one embodiment, Bluetooth pairing can exist in different states. For example a device can be in a "paired" state once the pairing procedure is successfully completed. A user-friendly procedure can be followed to pair devices. For example, in one embodiment, a user can pair a device by turning on the device, pressing and holding an "establish" button for a set amount of time, and then releasing the establish button, initiating the pairing procedure on the end user Bluetooth device; pressing and releasing the establish button on the measuring device, and pressing the appropriate button on the end user Bluetooth device. Of course, the claimed subject matter is not limited in this regard, and additional or alternate steps can be included for effecting the pairing. Visual confirmation of a successful pairing can be communicated to the user through operation of one or more display elements, such as causing one or more LEDs to blink slowly, for example. An embodiment may remain in an unpaired state if the device has not been paired or if the pairing procedure failed.

One or more batteries providing power to a device in one embodiment can also exist, at any given time, in one or more of multiple possible states. For example a battery can be in "normal operation" if it is ready to use. This state can be achieved when an external power source is disconnected from charge contacts on the embodiment. One or more LED(s) or other display elements can be lit or activated to signify the normal operation state. An embodiment can also enter a "charging" state when charge contacts are connected to an external power source. As one example of a visual indicator of this state, one or more LEDs can be caused to blink in a manner that would be substantially visually perceived as slowly blinking while the device is charging, as but one example. The illuminated LEDs can also exhibit constant illumination (i.e., non-blinking) when the battery is fully charged. Use of a device can be prohibited or limited while the device is charging. A "low battery" state can also be visually indicated. For example, one embodiment can employ one or more slowly blinking LEDs to convey the low battery state. An embodiment can enter the low battery state when a predetermined, known amount of battery power remains, thus informing a user of approximate remaining power. A battery embodiment can enter a "substantially empty" battery state when the battery's energy has been drained to a specified level. An embodiment can indicate this condition to the user by a omitting a response to button selection, as well as presenting no illuminated or active displays. In the substantially empty battery state, the primary option available to the user is to charge the battery.

Those having skill in the art will recognize that many changes may be made to the details of the above-described embodiments without departing from the underlying principles of the invention. The scope of the present invention should, therefore, be determined only with reference to the claimed subject matter.

The invention claimed is:

1. An auscultation system comprising:
(a) a chest-piece ergonomically shaped for single hand operation having a nonmetallic contact surface to be placed in contact with a subject, a microphone built into said chest-piece for detecting sound from said subject and converting said sound into an electrical signal, a plurality of filters built into said chest-piece to eliminate ambient noise and emphasize bell sounds, diaphragm sounds, and a combination of bell and diaphragm sounds of said electrical signal depending on an operation mode resulting in an enhanced electrical signal, a controller built into said chest-piece for electrically controlling said chest-piece, operation mode selector for selecting said operation mode, a wireless transmitter built into said chest-piece for wirelessly transmitting said enhanced electrical signal to a wireless receiver, a battery-based power source, and
(b) a wireless receiver piece for examination of said enhanced electrical signal, said wireless receiver piece comprising a built-in wireless receiver and a power source.

2. The auscultation system of claim 1, wherein said auscultation system further comprises a plurality of communication interfaces including a wireless communication interface, an audio jack, or an audio transmission conduit, and the wireless communication interface is configured for transmitting the processed signal substantially in accordance with a BLUETOOTH wireless communications standard.

3. The auscultation system of claim 1, wherein said receiver is chosen from a group including: a wired or wireless headphone, speaker, computer, PDA, table PC, mobile communication device, hearing aid device, and ear bud.

4. The auscultation device of claim 1, wherein said wireless receiver is not a stethoscope.

5. The auscultation system of claim 1, wherein said receiver is a wireless mobile device with real-time waveform visualization, analysis, processing, and storage capabilities.

6. The auscultation device of claim 5, wherein said wireless mobile device is a tablet.

* * * * *